United States Patent [19]

Ramsay et al.

[11] 4,040,697
[45] Aug. 9, 1977

[54] ELECTRICAL CONNECTOR

[75] Inventors: Donald C. Ramsay, Braintree; James M. Tantillo, Brockton, both of Mass.

[73] Assignee: Component Manufacturing Service, Inc., West Bridgewater, Mass.

[21] Appl. No.: 674,397

[22] Filed: Apr. 7, 1976

[51] Int. Cl.² .......................................... H01R 11/22
[52] U.S. Cl. .............................. 339/61 R; 339/200 P; 339/255 P
[58] Field of Search ............ 339/61 R, 108, 110, 339/149-151, 200 P, 218 R, 228, 255 P, 260, 261; 24/137 R, 255 R

[56] References Cited

U.S. PATENT DOCUMENTS

| 2,103,891 | 12/1937 | Brown | 339/255 P |
| 3,624,590 | 11/1971 | Bolduc | 339/255 P |
| 3,774,143 | 11/1973 | Lopin | 339/61 R |
| 3,842,394 | 10/1974 | Bolduc | 339/255 P |

Primary Examiner—Roy Lake
Assistant Examiner—Neil Abrams
Attorney, Agent, or Firm—Wolf, Greenfield & Sacks

[57] ABSTRACT

An electrical connector has a resilient, stamped, metallic leaf contact defining a narrow neck contact entrance area and having reversely bent ends on either side of said area. A plastic body section embeds the ends and spans the area to provide two side by side lever legs arranged to act so that pressure on the legs resiliently opens the narrow neck to allow entrance of a second body contact. Relaxation of pressure on the legs causes resilient action of the connector to provide gripping of the second contact with a positive three point grip.

6 Claims, 5 Drawing Figures

ELECTRICAL CONNECTOR

BACKGROUND OF THE INVENTION

Many electrical connectors are known for allowing connections between body electrodes of conventional types and an electrical monitoring machine such as a electrocardiograph machine. Such connectors are often in the form of small gripper which have various contacts formed to resiliently grip the body electrode in a variety of ways. Many such grippers are suitable for various purposes but have one or more problems, as for example, lack of sufficient gripping force, difficulties in manufacture and or complexity of use. One know connector is disclosed in U.S. Pat. No. 3,774,143 which has a particular metal contact member embedded in a plastic to provide for contact action. That connector requires certain manufacturing procedures which are different from the simple stamping of contacts and such connectors may not have maximized contact pressure and area between the electrode and the metal contact of a monitoring machine.

SUMMARY OF THE INVENTION

It is an object of the present invention to provide an electrical connector which is useful to connect an electrical lead to a body electrode rapidly and efficiently with good electrical contact and desired contact pressure so as to resist accidental removal.

It is still another object of this invention to provide an electrical connector in accordance with the preceding object which connector is easily cleaned to allow maintenance of good surface contact over long life of the connectors.

It is still another object of this invention to provide an electrical connector in accordance with the preceding objects which can be disposable if desired and which is formed of low cost stamped metals as the contact member.

According to the invention an electrical connector comprises a resilient, metallic leaf, stamped, contact defining a narrow neck contact entrance area and preferably having plastic gripping ends, and reversely bent ends, on either side of the area. A plastic body section, preferably of polypropylene or similar material, embeds the ends and provides two side by side legs extending from the area arranged to act as levers so that pressure on said legs resiliently opens the narrow neck to allow entrance of a second contact or electrode contact and relaxation of pressure causes resilient action of said connector to provide gripping of said second contact by the metal leaf, stamped contact.

Preferably the metallic leaf connector is a bent strip of a resilient spring metal and has a trapezoidal electrode holding area with a plurality of forming detents arranged to give at least three point contact with a conventional metallic body electrode contact.

It is a feature of this invention that the connector can be economically produced since it is a stamped contact and can be molded in a single operation of molding plastic around the metal contact. Good surface contact can easily be obtained by suitably dimpling the metal leaf at three points about a body electrode contact. The leaf contact can be easily cleaned to maintain good surface contact ability. The units can be semi-disposable since they are inexpensively formed. Plastics such as Delrin or polypropylene can be used so that the leaf contact can be autoclaved without difficulty. Preferably the contact area is a reentrant area so that the electrode contact grasped is always resiliently urged against a metallic surface preferably at three points of contact. In certain embodiments, non-tangling features can be incorporated as well as positioning means with respect to conventional body electrodes.

BRIEF DESCRIPTION OF THE DRAWINGS

The above and other features, objects and advantages of the present invention will be better understood from the following specification when read in conjunction with the attached drawings in which.

DECRIPTION OF PREFERRED EMBODIMENTS

Figure 1:
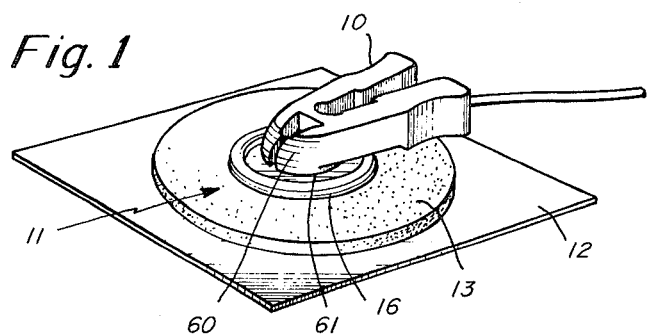
FIG. 1 is a perspective view of an electrical connector in accordance with this invention attached to a conventional body electrode.

With reference now to the drawings, a preferred connector 10 is illustrated in FIG. 1 attached to a conventional body electrode assembly 11.

The body electrode assembly 11 has an adhesive undersurface covered by protective sheet 12 which is removed when the electrode is attached to the body as known in the art. The electrode base 13 is a rubbery material mounting a conventional metallic electrode contact 14 with an annular top ridge 15 adapted to be gripped by the contact of the connector. A surrounding annular rib 16 is raised from the base 13 of the conventional electrode.

Figure 2:
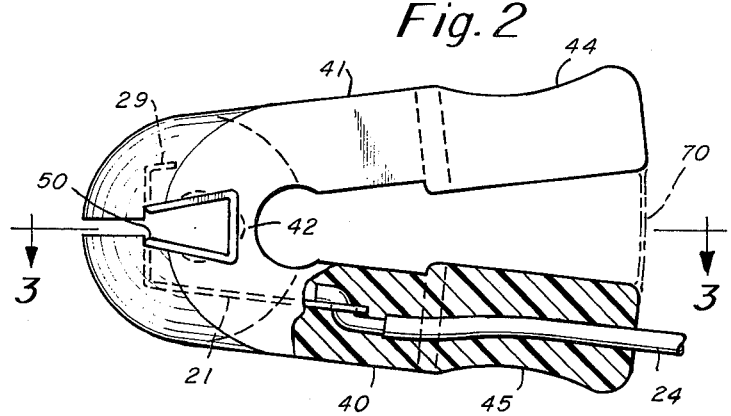
FIG. 2 is a bottom view of the connector with one leg partially in cross-section.
Figure 3:
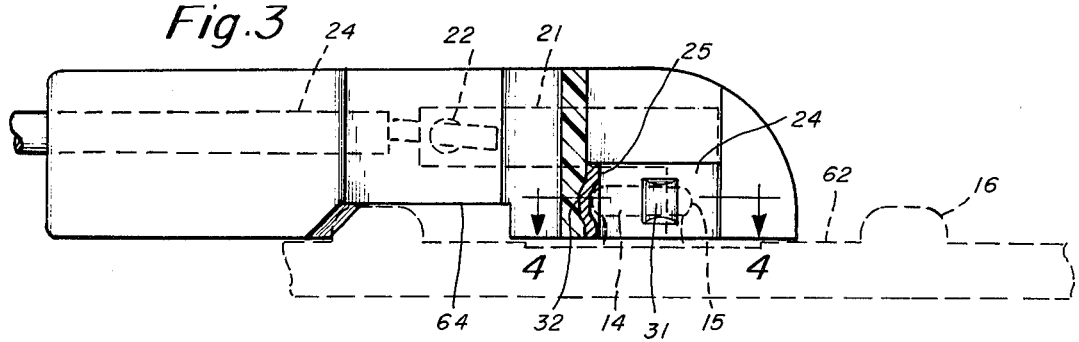
FIG. 3 is a side view partially in cross-section.
Figure 4:
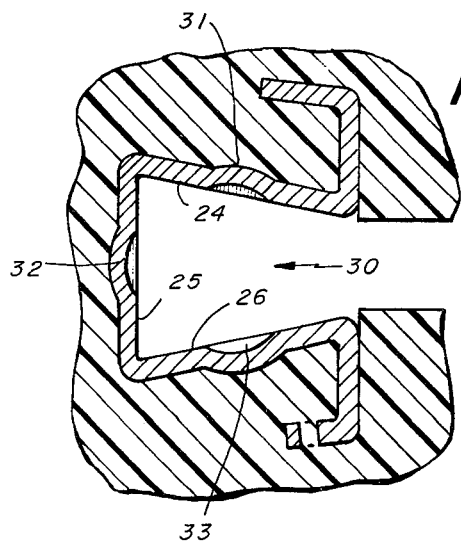
FIG. 4 is a cross-sectional view taken through line 4—4.

The connector 10 incorporates a resilient, spring, metallic stamping 20 which is stamped from conventional metal contact material such as 0.015 inch thick spring tempered phosphor bronze. It is in leaf form having a first leg 21 with a suitable hole 22 for soldering of a lead wire 24 as known in the art. Hole 23 aids in embedding the contact. Walls 24, 25, and 26 are arranged in a trapezoidal form and are joined to the leg 21 by wing wall 27 while wing wall 28 with its reversely bent portion 29 extends from the contact area formed by the trapezoidal arranged walls. The metal contact 20 is stamped in conventional contact stamping procedures. It has a resiliency such that it tends to return to its original form shown in FIGS. 2 and 5. The angles of the inner end of the trapezoidal area are preferably equal and are designed to provide, with the resiliency of the metal, a spring force on the electrode 14 tending to push the electrode contact in the direction of arrow 30 as best shown in FIG. 4. Thus when an electrode is gripped in three detents or dimples 31, 32, and 33 on the walls 24, 25, and 26, resilient spring action urges the electrode into the dimples of the contact with a good holding force providing for good electrical surface to surface contact with the electrode. The dimples are spaced in between the top and bottom edges of the arranged walls in conformity with the expected height of the rim 15 of the electrode contact. The dimples are designed to provide a positve locking action with the electrode requiring resilient spreading of the trapezoidal form to remove the contact from the electrode. Preferably a minimum of five pounds of pull is required to pull the contact 20 from the electrode contact without first applying a gripping and spreading force thus minimizing the chance of accidental disconnection.

Figure 5:
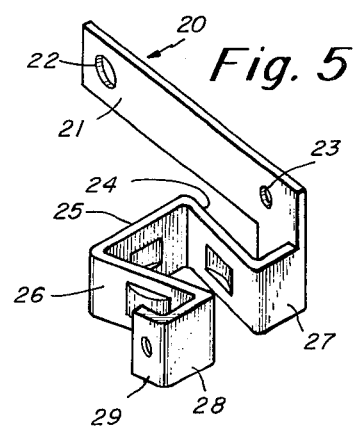
FIG. 5 is a perspective view of contact element of the preferred connector of this invention.

The connector is formed in a conventional integral molding step where the plastic is molded directly about the contact of FIG. 5 to form the double legs 40, 41 opposed to each other and extending forwardly with an interconnection at 42. Interconnection 42 preferably aids in the resilient action of the contact due to the inherent resiliency of the plastic particularly when material such as polypropylene and Delrin are used. Plastic or other insulating material that will not take a permanent set is preferred in the electrode in order to maximize resiliency. Moreover autoclavical plastics are preferred to allow reuse where desired. The plastic legs provide side indented finger gripping portion 44, 45 which aids in enabling finger pressure to squeeze the legs together to cause resilient opening of the narrow contact entrance portion 50 to enable the connector to be slid over an electrode and to grasp the electrode when the finger pressure is released due to resilient spring contact.

The top side of the plastic body of the connector, as shown at FIG. 1, has a rounded nose portion 60 to prevent snagging. A lower extending integral boss 61 is designed to mate with a flat area of a conventional electrode as shown at 62 to align the contact leaf member with its detents 31, 32 and 33 in a plane parallel to surface 62 and positioned to grip the rim 15. Preferably a cut out 64 is provided in the bottom surface of the connector body to position the metal contact parallel to the flat surface of the electrode base 13 by use of mating contact with the rim 16.

In the preferred embodiment, the angles at the base of the trapezoidal portion are 10° with the opening 50 being 0.100 inch and the wall 25 having a length of 0.2 inch and all of the walls having a top to bottom height of 0.125 inches. The plastic has a top to bottom height at the boss 61 of 0.280 inches with each leg having a rearward extension from the front edge of 1.040 inch. These dimensions are variable depending upon the design of the electrode to be contacted and the particular materials used.

While a specific embodiment of this invention has been shown and described, many variations are possible. For example, in one form of the invention a thin web diagrammatically shown at 70 is intergrally molded with the ends of the legs and is yieldable when the legs are pressed together. This web acts to prevent tangling of the connectors with the line cords or leads 24 by preventing entrance of the leads between the legs.

The specific dimensions of the connectors used can vary greatly as can the outer shapes. In all cases, a relatively stiff plastic is used which aids in resiliency of the contact along with a resilient stamped metallic embedded contact. Preferably three points of indentation or contact with an electrode are provided in a reentrant or entrance narrow area metal leaf contact although in some cases two or more contact points need be used. The specific shape of the contact area formed by the leaf contact can vary. For example it may be circular or of other forms although the trapezoidal form is preferred for ease of manufacture and maximized efficiency. Reverse bends in the metal contact are preferred to provide for interlocking of the plastic and metal to form a substantially integral unit although in some cases other interlocking means could be used. For example holes in wing portions 27 and 28 could provide anchoring when embedded in the resilient insulating material of the body. While a web 70 has been described other wire blocking means can be used if desired. For example each of said leg ends could carry overlapping inwardly extending pins or tabs to bar entrance of lead wires between the legs.

We claim:

1. An electrical connector comprising a resilient metallic stamped contact defining a narrow neck reentrant contact area entrance and having extension ends on either side of said area carrying means for engaging a plastic body,
    a plastic body section embedding said extension ends and providing two side by side legs extending from said area arranged to act as levers so that pressure on said legs resiliently opens said narrow neck to allow entrance of an electrode contact and relaxation of pressure cause resilient spring action of said stamped contact to provide gripping of said electrode,
    said stamped contact defining wall means carrying three detents positioned so that said resilient action provides positive gripping of said electrode with said electrode urged into engagement with each of said three detents of said resilient contact, said wall means having sections converging towards each other in the direction of said reentrant contact area entrance.

2. An electrical connector in accordance with claim 1 wherein said stamped contact defines integral opposed reversely bent portions.

3. An electrical connector in accordance with claim 2 and further comprising,
    said plastic being a resilient material having a stiffness and resiliency which allows expansion and contraction of said contact area without taking a permanent set,
    said wall means comprising three wall sections in a trapezoidal arrangement.

4. An electrical connector in accordance with claim 1 and further comprising,
    said body section defining a lower surface designed to coact with an electrode assembly to position said detents in a plane for maximized gripping of a rim provided by said electrode.

5. An electrical connector in accordance with claim 1 and further comprising,
    said side legs having rear ends,
    said ends carrying a resilient web extending therebetween and integrally molded therewith acting to prevent entrance therebetween of lead wires which could cause intertangling of said connectors with said wires.

6. An electrical connector comprising a resilient metallic stamped contact defining a narrow neck contact area entrance and having extension ends on either side of said area carrying means for engaging a plastic body,
    a plastic body section embedding said extension ends and providing two side by side legs extending from said area arranged to act as levers so that pressure on said legs resiliently opens said narrow neck to allow entrance of an electrode contact and relaxation of pressure cause resilient action of said stamped contact to provide gripping of said electrode,
    said side legs having ends,
    said ends carrying a resilient web extending therebetween and integrally molded therewith acting to prevent entrance therebetween of lead wires which could cause intertangling of said connectors with said wires.

* * * * *